United States Patent [19]
DeBusk et al.

[11] Patent Number: 5,628,724
[45] Date of Patent: May 13, 1997

[54] WOUND DRESSING AND DELIVERY SYSTEM THEREFOR

[75] Inventors: Janet S. DeBusk; Randel B. Holmes, both of Knoxville, Tenn.

[73] Assignee: DeRoyal Industries, Inc., Powell, Tenn.

[21] Appl. No.: 365,747

[22] Filed: Dec. 29, 1994

[51] Int. Cl.$^6$ .................................................. A61F 13/00
[52] U.S. Cl. ........................... 602/58; 602/52; 602/57; 604/180; 206/440; 428/354; 428/41.7
[58] Field of Search ........................... 602/42, 43, 52, 602/54, 57; 206/440, 441, 904; 604/304, 307, 180; 428/343, 352, 354, 355, 351

[56] References Cited

U.S. PATENT DOCUMENTS

| | | | |
|---|---|---|---|
| Re. 24,906 | 12/1960 | Ulrich | 602/54 |
| Re. 33,727 | 10/1991 | Sims | 602/43 X |
| 4,499,896 | 2/1985 | Heinecke | 602/46 X |
| 4,600,001 | 7/1986 | Gilman | 128/156 |
| 4,614,183 | 9/1986 | McCracken et al. | 128/132 |
| 4,706,662 | 11/1987 | Thompson | 128/155 |
| 4,753,232 | 6/1988 | Ward | 602/42 X |
| 4,854,995 | 8/1989 | Kasper et al. | 156/243 |
| 4,917,928 | 4/1990 | Heinecke | 428/41 |
| 4,928,680 | 5/1990 | Sandbank | 128/155 |
| 5,088,483 | 2/1992 | Heinecke | 602/46 |
| 5,153,040 | 10/1992 | Faasse, Jr. | 428/40 |
| 5,160,315 | 11/1992 | Heinecke et al. | 602/57 |

FOREIGN PATENT DOCUMENTS

| | | | |
|---|---|---|---|
| 2120104 | 5/1982 | United Kingdom | 602/42 X |
| 2131299 | 10/1982 | United Kingdom | 602/42 X |

*Primary Examiner*—Corrine M. McDermott
*Assistant Examiner*—Chalin Smith
*Attorney, Agent, or Firm*—Luedeka, Neely & Graham, P.C.

[57] ABSTRACT

An improved wound dressing composite is disclosed, having a membrane film wound dressing, a relatively stiff substantially planar carrier sheet with tabs, and a releasable cover. The film dressing has an upper surface, a lower adhesive surface and opposed side edges for application in a spread out disposition to a wound site with the lower surface adhered thereto. The film dressing, being relatively thin, is substantially unable to support itself in a planar configuration. The carrier sheet has an upper surface, a lower surface, and opposed edges. The carrier sheet is releasably adhered on its lower surface to the upper surface of the film dressing in supporting relation for supporting the film dressing in a planar configuration, with the side edges of the film dressing and carrier sheet generally aligned in close adjacency. At least one tab is attached to the carrier sheet adjacent at least one of the side edges thereof, and extends out beyond the side edge of the carrier sheet and the adjacent side edge of the film dressing. The tab is used to remove the carrier sheet from the film dressing after application. A cover protects the lower adhesive surface of the film dressing prior to application, and is used to hold the composite during application.

25 Claims, 3 Drawing Sheets

5,628,724

WOUND DRESSING AND DELIVERY SYSTEM THEREFOR

FIELD OF THE INVENTION

The invention relates to wound dressings in general, and more particularly to improved delivery systems for such wound dressings.

BACKGROUND

Transparent membranes of thin polymeric films are well known in the art for their use as wound dressings. They are highly desirable because they allow passage of a controllable rate of moisture out of the wound site, and passage of a controllable rate of air into the wound site. Additionally, materials of this type will not allow liquids or pathogens such as bacteria to readily permeate through the membrane.

To achieve this balance of properties, the membranes have had to be extremely thin. Such thin membranes lack sufficient independent rigidity, and unless they are supported in some manner during application to the wound site, they tend to fold upon themselves. This problem is further compounded by the fact that such dressings have an adhesive on one surface to adhere the dressing to the wound site. When the dressing folds upon itself, the adhesive causes the dressing to stick together. Due to the thin nature of the membrane, it is difficult to peel the dressing apart and apply it to the wound site in a proper manner. Under conditions of dire medical emergency, the dressing may need to be applied quickly and accurately and current products do not lend themselves to rapid, accurate placement in such situations.

An object of the invention, therefore, is to provide a membrane film dressing with an improved delivery system.

Another object of the invention is to provide a membrane film wound dressing and a delivery system therefor which can be applied accurately and rapidly to a wound site with a minimum of steps.

Still another object of the invention is to provide a transparent gas and moisture vapor permeable, and liquid impermeable, membrane film dressing and a delivery system therefor which is relatively simple and inexpensive to manufacture and convenient to use.

Other objects of the invention will be evident from the ensuing description and appended claims.

SUMMARY OF INVENTION

With regard to the foregoing and other objects, the invention provides a wound dressing composite. In general, the composite comprises a membrane film wound dressing having an upper surface, a lower adhesive surface and opposed side edges for application in a spread out disposition to a wound site with the lower surface adhered thereto. The film dressing, being relatively thin, is unable to support itself in a planar configuration.

A relatively stiff, substantially planar carrier in sheet form having an upper surface, a lower surface, and opposed side edges, is releasably adhered on its lower surface to the upper surface of the film dressing in supporting relation for supporting the film dressing in a planar configuration with the side edges of the film dressing and carrier generally aligned in close adjacency.

At least one tab is attached to at least one of the opposed side edges of the carrier sheet. The tab extends outward beyond the side edge of the carrier and the adjacent side edge of the film dressing. The tab is used to remove the carrier from the film dressing after the dressing has been applied to the wound site.

A cover protects the lower adhesive surface of the film dressing prior to application. The cover is releasably adhered to the lower adhesive surface of the film dressing in covering relationship therewith.

In a preferred embodiment, at least one rigidity strip is disposed on the film dressing, having a width that is relatively narrow compared to the width of the dressing and a length that is substantially equal to the length of the dressing. The rigidity strip is preferably adherently disposed along the upper surface of the film dressing along the side edge which is adjacent the tab on the carrier. Alternately, the strip may be adherently disposed on the lower surface adjacent the same side edge, in which case the strip would include an adhesive coating on it's lower or exposed surface. An advantage of the rigidity strip is that it promotes adhesion between the wound dressing and the wound site when the carrier film is removed from the wound dressing by lifting up on the tab.

In a further embodiment, the rigidity strip may be disposed along the entire perimeter of the film dressing rather than along just a single side edge of the dressing. Alternately, there may be two rigidity strips, one along each of two opposing side edges of the dressing. As mentioned above, in any of the alternate embodiments, the rigidity strip may be located on either the upper or lower surface of the film dressing, or on both the upper and lower surfaces.

In a preferred embodiment, the rigidity strip is made of the same material as the film dressing, which is preferably a transparent polyurethane film, with a moisture vapor transmission rate (MVTR) greater than about 20 grams/100 in$^2$/24 hrs at 100° F. and 90% relative humidity as determined by ASTM E96 Method E, and which is preferably liquid and bacteria impermeable. The adhesive coatings on the film dressing and rigidity strip are preferably made of a hypoallergenic acrylate copolymer.

In alternate embodiments, the composite may have a generally rectangular shape with either sharp or rounded corners. In a further embodiment there may be a pad adhered to a center region of the adhesive lower surface of the film dressing. In a preferred embodiment, the carrier sheet is made of a transparent material so that the wound site is visible through the carrier and the film dressing during application.

BRIEF DESCRIPTION OF DRAWINGS

Additional aspects of the invention will become known from the following detailed description of preferred embodiments when considered in conjunction with the accompanying drawings, in which.

DETAILED DESCRIPTION OF INVENTION

Figure 1:
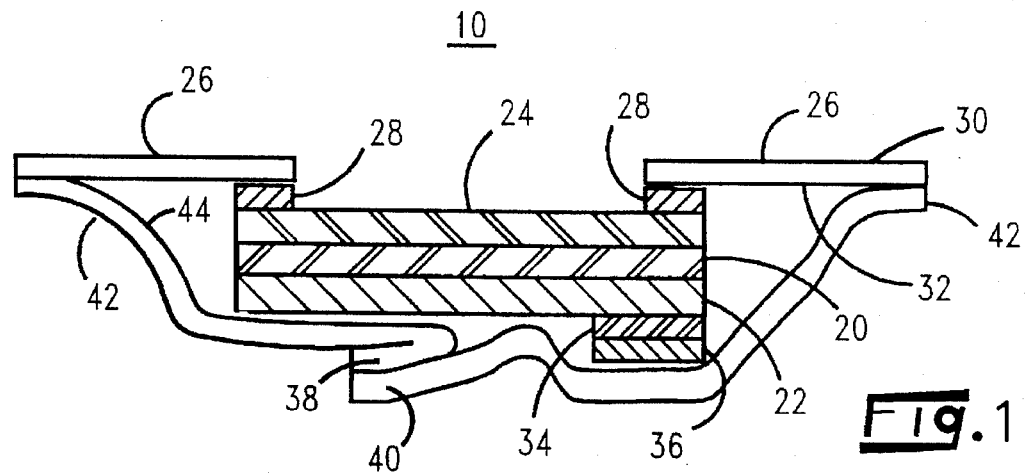
FIG. 1 is a front elevation cross-sectional view, not to scale, of one embodiment of a wound dressing composite according to the invention.

Referring now to the drawings in which like reference characters designate like or corresponding parts throughout the several views, there is shown in FIG. 1 a preferred embodiment of a wound dressing composite 10 according to the invention. It will be appreciated that the various elements of the composite 10 have not been drawn to scale. Particularly, the thicknesses of the various elements have been exaggerated with respect to the other dimensions, so that the lay-up of the composite may be better understood.

The composite includes a film dressing 20 which is to be applied over a wound site. The dressing 20 may be made from a variety of thin, transparent, polymeric membranes, such as polyurethane, elastomeric polyester, polyethylene, blends of polyurethane and polyester, chlorinated polyethylene, and polyetherpolyamide block copolymers or copolyesters. In a preferred embodiment, the dressing is made of 1 mil transparent polyurethane, such as that available from Medco Adhesive Products Co. of Bedford, Ohio under the trade name PRODUCT #8144. Thicknesses in the range of between about 0.80 mils to about 1.20 mils, and preferably between about 0.85 mils to about 1.15 mils, may be used. It is preferred that the dressing have a matte finish.

The MVTR of the finished dressing is dependant on the film thickness and the adhesive used for the film. A relatively high MVTR is very desirable, because it renders the dressing 20 substantially non-occlusive, meaning that any liquids which may seep from the wound will be able to evaporate from the wound site at a rate sufficient to keep the wound from pooling with liquid, but also at a rate low enough to keep the wound from drying out completely. A balance between these extremes provides a condition which is optimal for wound healing.

Typical MVTR rates range from an average of about 28.3 grams/100 in$^2$/24 hrs for POLYSKIN II from The Kendall Company of Boston, Mass. to about 44.5 grams/100 in$^2$/24 hrs for OPSITE 3000 from T. J. Smith and Nephew Medical Limited of Hull, England to about 51 grams/100 in$^2$/24 hrs for TEGADERM HP from Medical-Surgical Division/3M of St. Paul, Minn. to about 82.7 grams/100 in$^2$/24 hrs for TRANSEAL 46-303 from DeRoyal Industries, Inc. of Powell, Tenn.

Additionally, the nature of the dressing 20 prevents the permeation of liquids through the membrane, so that no liquid from external sources may gain access to the wound site. Also, the dressing 20 is impermeable to bacteria, thus maintaining the antiseptic condition of a cleaned wound site, and preventing infection and other complications to wound healing.

While the dressing 20 may be manufactured in any desired size or shape, in the preferred embodiments of the invention square or rectangular dressings in sizes of from about 1.75 by 1.75 inches and about 8 by 12 inches are used.

The lower surface of the dressing 20 is coated with an adhesive 22 for adhering the dressing 20 to a wound site. The adhesive 22 is preferably a hypoallergenic acrylate copolymer, preferably of the type available from Monsanto Company of St. Louis, Mo. under the trade name of GELVA. Other adhesives, such as polyvinyl ethers, may also be used. The thickness of the adhesive 22 may be from about 0.4 mils to about 0.8 mils, and is preferably from about 0.5 mils to about 0.7 mils. Of great importance is the ability of the adhesive 22 to provide a firm, continuous adhesion to a wound site, normally human skin, such that the dressing 20 will not readily peel away from the wound site during normal use, and yet will release without undue complication when the dressing 20 is no longer required. Additionally, the adhesive 22 should be of a material that will not unduly impede the healing process, restrict vapor transmission or cause adverse reactions with human tissue.

Releasably adhered to the upper surface of the film dressing 22 is a carrier sheet 24. In the preferred embodiment, the dressing 20 is extruded onto a silicon-coated lower surface of the carrier sheet 24. The carrier sheet 24 is preferably transparent, like the dressing 20, so that the wound site may be seen through the carrier film 24 and the film dressing 20 during application of the dressing to the wound site.

It is a feature of the invention that the carrier sheet 24 is substantially rigid in relation to the film dressing 20 to support the dressing in a relatively smooth, planar configuration for application to the site. However, the sheet 24 is sufficiently flexible and drapeable to yieldably conform to skin surface undulations and contours so that the supported film 20 may be pressed onto firm, continuous engagement with the skin for adherence over the area irrespective of dimensional irregularities, while supported in a spread out unwrinkled configuration by the sheet 24.

These properties are preferably provided through use of transparent films of polyolefins, polypropylene, polyethylene, or polyester with a thickness in the range of from about 2 to about 3 mil. In the preferred embodiment, a film of 2 mil transparent polyethylene laminating film is used which is available from Deerfield Company of S. Deerfield, Mass. The length and width dimensions of the carrier sheet 24 are preferably chosen to at least match those of the dressing 20. Most preferably, the side edges of the sheet 24 and film 20 are coextensive.

Tabs 26 are attached to the carrier sheet 24 by an adhesive 28. In a preferred embodiment, the tabs 26 are made of paper with a high gloss coating on an outer surface 30 and a plain or uncoated inner surface 32, but may alternately be made of any other material with a stiffness sufficient to act as a handle for gripping between the finger and thumb. The tabs 26 are used to remove the carrier sheet 24 from the film dressing 20 after application to the wound site, as will be explained in greater detail below.

In a preferred embodiment, a rigidity strip 34 is applied to the adhesive 22 on the surface of the film dressing 20. The strip 34 is preferably relatively narrow, having a width ranging from about 0.05 to about 0.3 times the width of the dressing 20, but is about the same length as one edge of the dressing 20. The strip 34 is preferably made of the same material as the dressing 20, and has an adhesive 36 on its lower surface, the adhesive 36 being of the same composition as the adhesive 22 on the lower surface of the dressing 20. Since the strip 34 is preferably made of the same material as the dressing 20, and is also transparent, it is virtually invisible on the wound site.

The strip 34 is preferably placed on the film dressing 20 so that it is along a side edge portion of the dressing 20, under that portion of the tab 26 that is adhered to the carrier sheet 24. The strip 34 aids in adhering the film dressing 20 to the wound site during removal of the carrier sheet 24, as will be explained in greater detail below.

Extending across the entire width and length of the composite, including the tabs 26, the adhesive 36 under the strip 34, and the adhesive 22 under the dressing 20, are inwardly overlapping sections 38 and 40 of a cover 42. The sections 38 and 40 of cover 42 are preferably made of paper, with a release coating 44 or other surface treatment which limits adherence of sections 38 and 40 to the adhesives 22 and 36 against an effort to pull the sections 38 and 40 from the composite. The coating 44 is preferably silicone, although any medically acceptable coating which forms a releasable attachment to the adhesives 22 and 36 may be used.

The cover 42 protects the adhesives layers 22 and 36 in at least two ways. First, it prevents the adhesives 22 and 36 from coming into contact with contaminants that may infect the wound. Second, the cover 42 helps to preserve the adhesive nature of the adhesives 22 and 36 so they will readily adhere to the wound site. The cover 42 may also be used to assist in applying the film dressing 20 to the wound site in one embodiment, as explained in greater detail below.

Figure 2:
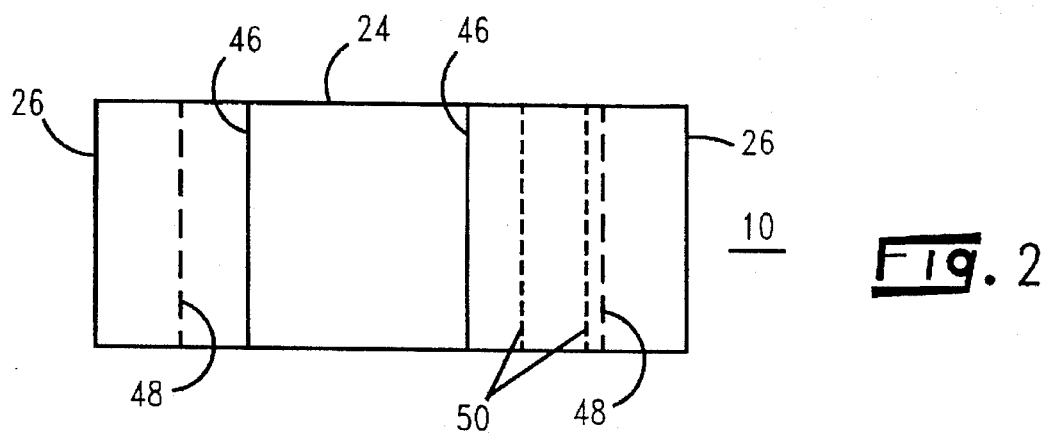
FIG. 2 is a top plan view of the composite of FIG. 1.

In FIG. 2 there is shown a top view of the composite 10 of FIG. 1 described above. Seen at either end of the composite 10 are the tabs 26 terminating with inner edges 46, so that a portion of each tab 26 overlies the carrier sheet 24 illustrated by the space between tab edges 46 and carrier film side edges 48. Edges 50 of the strip 34 disposed on the dressing 20 are illustrated, showing that the outer edge is preferably aligned with the outer edge of the sheet 24 and the edge of the film 20.

Figure 3:
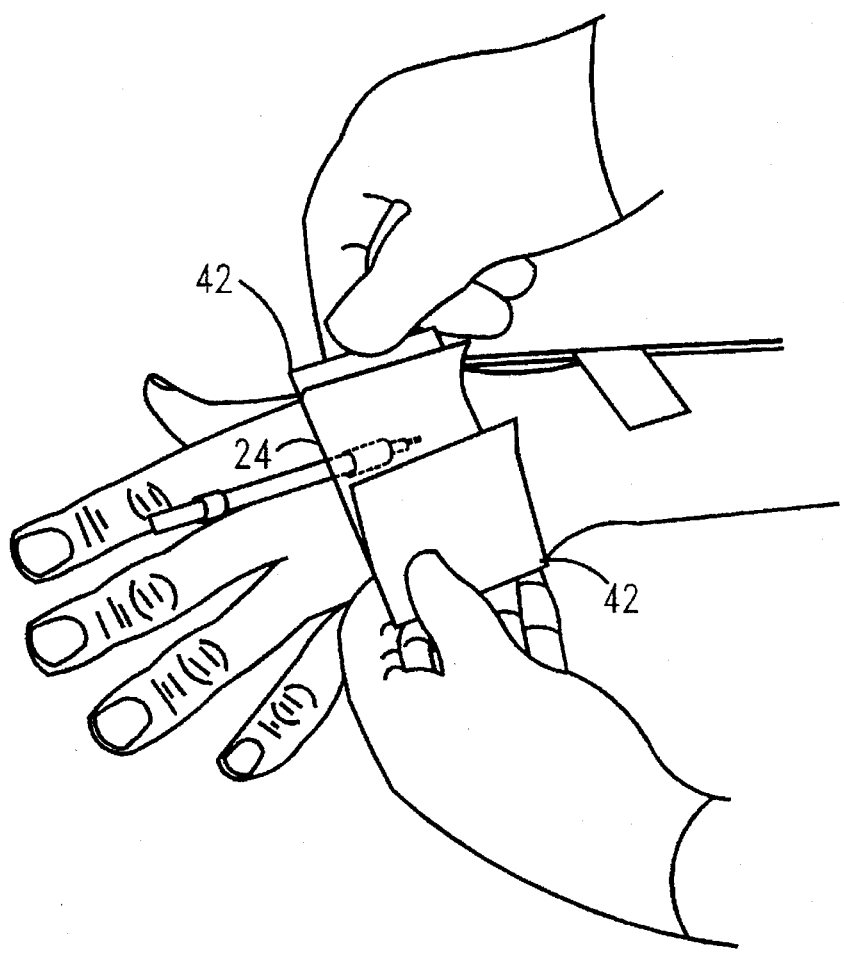
FIGS. 3 and 4 depict one method of applying the wound dressing.
Figure 4:
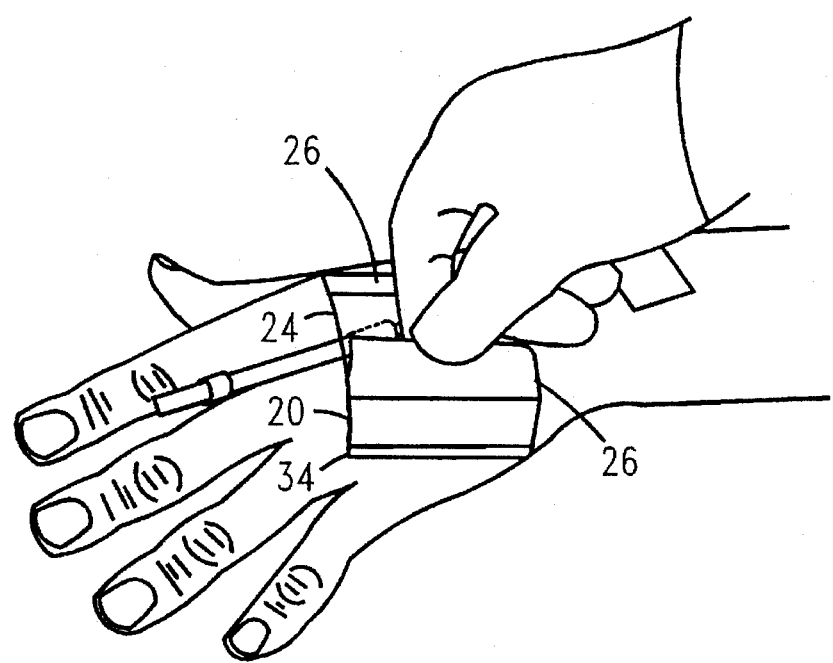

One method of applying the composite 10 to a wound site is illustrated in FIGS. 3 and 4. The sections 38 and 40 of cover 42 are grasped at their edges nearest the center of the width of the composite 10. The adhesives 22 and 36 are oriented toward the wound site which is visible through the carrier sheet 24 and the film dressing 20. As the edges of the sections 38 and 40 are drawn apart, the exposed adhesives 22 and 36 are placed over the wound site, such as over the entrance of a catheter at an infusion site as shown. The sections of the cover 42 are pulled in an outward and downward motion, applying the film dressing 20 to the wound site, until the sections are removed completely from the composite 10.

The film dressing 20 is firmly adhered to the wound site by applying pressure to the composite 10, over the width of the carrier sheet 24, particularly at the edges. Next, as illustrated in FIG. 4, one of the tabs 26 may be grasped, preferably a tab 26 overlying the strip 34 if the strip 34 is present, and using the tab 26 as a handle, the carrier sheet 24 is lifted from the film dressing 20 moving from one side of the dressing 20 to the opposing side. This leaves the dressing 20 adhered to the wound site in a smooth unwrinkled disposition. In a preferred embodiment, the strip 34 helps keep the dressing 20 from being lifted up from the wound site as the carrier sheet 24 is removed. That is, because the strip 34 provides additional rigidity to the dressing 20 at the edge of the dressing 20 from which the carrier is lifted, the tendency of the dressing to peel away from the wound site as the carrier sheet 24 is removed is reduced.

Figure 5:
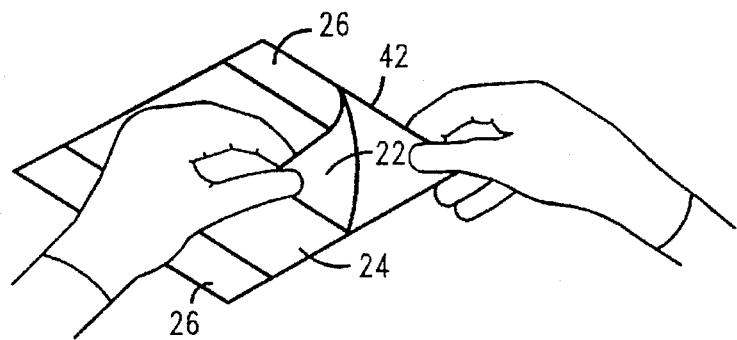
FIGS. 5, 6, and 7 depict an alternate method of applying the wound dressing.
Figure 6:
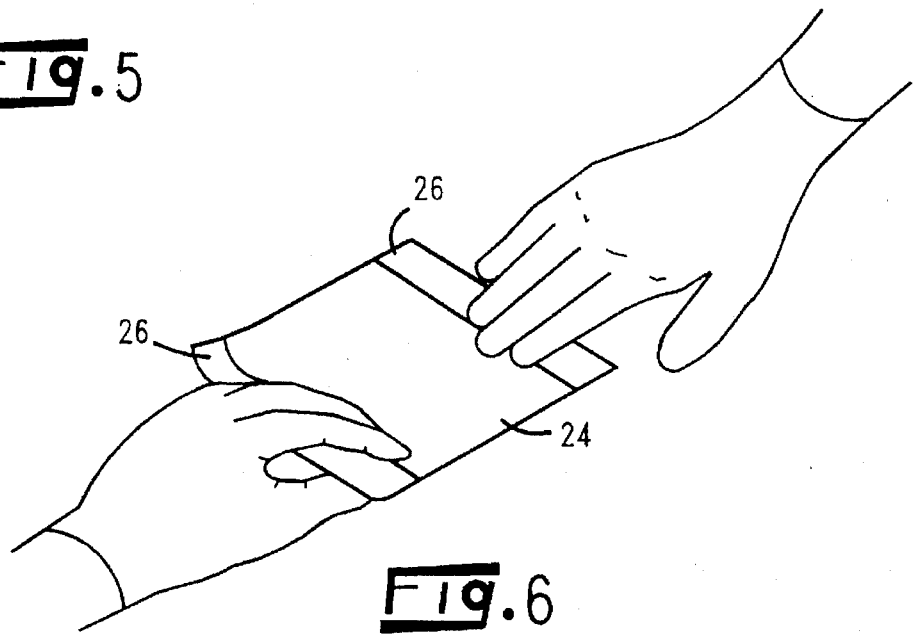
Figure 7:
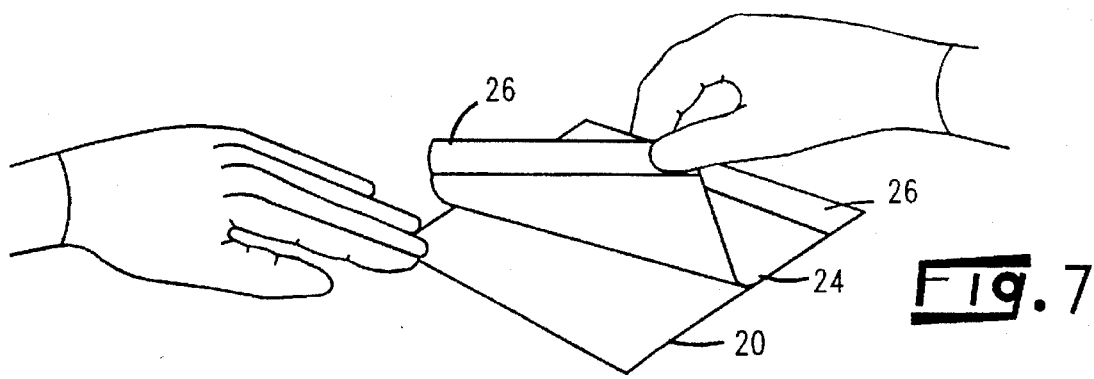

In an alternate method of applying the film dressing 20, as illustrated in FIGS. 5 through 7, the cover 42, which in this embodiment is a single sheet, is first peeled away from the composite 10 by grasping the tab 26 and the cover 42 in separate hands and pulling them apart, exposing the adhesive 22 (and adhesive 36 if the strip 34 is present and underneath the dressing 20).

As illustrated in FIG. 6, the composite 10, being held by the tabs 26, is then applied to the wound site by pressing the adhesives 22 and 36 to the wound site. Next, as shown in FIG. 7, the carrier sheet 24 is removed from the film dressing 20 by grasping one of the tabs 26 and removing the carrier sheet 24 in the same manner as described above with reference to FIG. 4.

Figure 8:
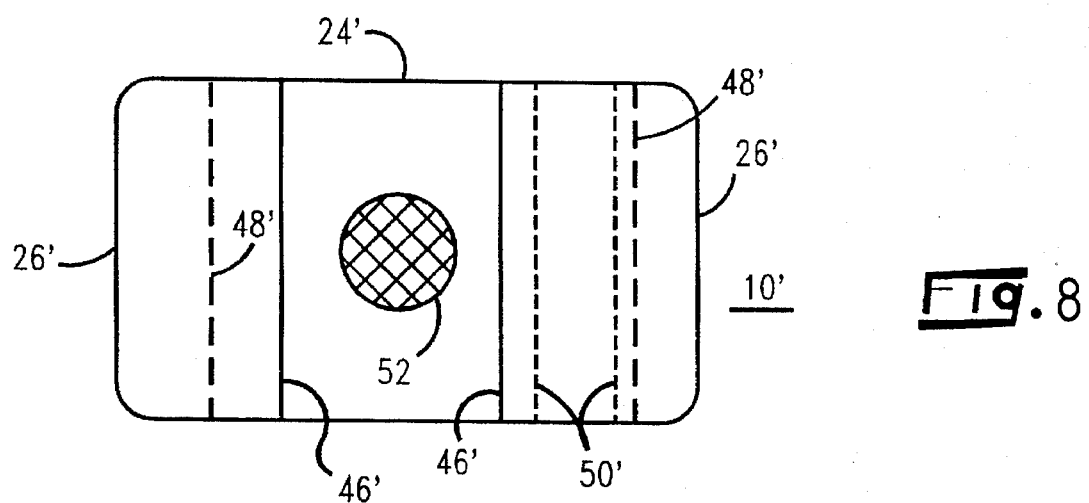
FIG. 8 is a plan view of an alternate shape of the composite.

In FIG. 8, there is shown an alternate embodiment 10' of the composite of the invention having rounded corners. Portions of the composite 10' which correspond to those of FIGS. 1 and 2 are identified with a prime suffix. An additional feature illustrated in FIG. 8 is pad 52, located in a central region of the composite 10' under the dressing 20'. The pad 52 is shown in a rounded configuration, but it may be any desired shape such as a square or rectangular configuration.

Figure 9:
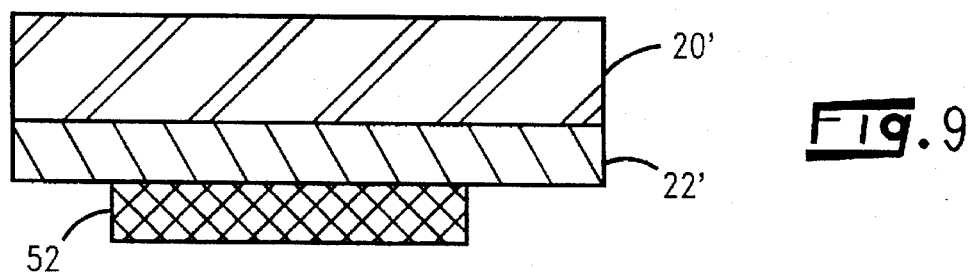
FIG. 9 is a cross-sectional view, not to scale, of the composite of FIG. 8.

The placement of the pad 52 is better illustrated in FIG. 9, depicting only the dressing 20', the adhesive 22', and the pad 52. Again, the thickness of the various elements in FIG. 9 have been greatly exaggerated so that the lay-up of the composite may be more easily understood.

The pad 52 is useful for absorbing drainage from the wound so that it will not accumulate on the skin during the time required to evaporate moisture through the film dressing 20'. The pad 52 may also provide an area where the adhesive 22' will not come in contact with the wound site, should it be undesirable to have an adhesive on the wound itself. Additionally, any one of a number of medications may be applied to the pad 52 before the film dressing 20' is applied to the wound site. Such medications may be useful, for example, to prevent infection, provide local anesthetic, or promote the healing process.

In one embodiment, the pad 52 is a gauze or batting of natural fibers such as cotton or synthetic fibers such as rayon or alginate. The size, shape, and placement of the pad 52 is open to multiple embodiments, depending upon the exact and varied requirements of the dressing. The pad 52 may also be provided by a hydrogel such as the polyvinylpyrolidone composition sold under trademark AQUASORB by DeRoyal Industries, Inc. of Powell, Tenn.

While preferred embodiments of the present invention have been described above, it will be appreciated by those of ordinary skill in the art that the invention is capable of numerous modifications, rearrangements and substitutions of parts without departing from the spirit of the invention.

What is claimed is:

1. A wound dressing composite which comprises:

a breathable membrane film wound dressing having an upper surface, a lower adhesive surface and opposed side edges for application in a spread out disposition to a wound site with the lower surface adhered thereto, said film dressing substantially unable to support itself in a planar configuration;

a relatively stiff substantially transparent integral film carrier sheet having an upper surface, a lower surface, and opposed side edges, the carrier sheet being releasably adhered on its lower surface to substantially the entire upper surface of the film dressing in supporting relation for supporting the entire film dressing in a planar configuration, with the side edges of the film dressing and carrier sheet generally aligned in close adjacency;

at least one tab substantially fixedly attached to the carrier sheet adjacent at least one of the opposed side edges thereof, the tab extending out beyond the side edge of the carrier sheet and adjacent a side edge of the film dressing for removing the carrier sheet from the film dressing after application thereof to the wound site;

a cover releasably adhered to the lower adhesive surface of the film dressing in covering relationship therewith for protecting the lower adhesive surface prior to application of the film dressing to the wound site; and a rigidity strip having a width which is relatively narrow compared to the width of the film dressing and having a length substantially equal to the length of the film dressing said strip being made of substantially the same material and having substantially the same thickness as said film dressing and being adjacent an edge of the film dressing along the side edge of the film dressing which is adjacent the tab for promoting adhesion between the film dressing and the wound site when the carrier sheet is removed from the film dressing, said rigidity strip and said film dressing each having a MVTR greater than about 20 grams/100 in$^2$/24 hours at 100° F. and 90% relative humidity as measured by ASTM E96 Method E.

2. The composite of claim 1 wherein the rigidity strip has an upper surface and a lower adhesive surface, the lower adhesive surface adhered to the upper surface of the film dressing.

3. The composite of claim 1 wherein the film dressing is further comprised of a transparent polyurethane film having moisture vapor transmission rates greater than about 20, and is essentially water and bacteria impermeable.

4. The composite of claim 1 wherein the lower adhesive surfaces of the film dressing and rigidity strip further comprise a hypoallergenic acrylate copolymer.

5. The composite of claim 1 wherein the tab is comprised of paper.

6. The composite of claim 1 wherein the film dressing further comprises a pad adhered to a center region of the adhesive lower surface of the film dressing.

7. The composite of claim 1 wherein the composite has a generally rectangular shape.

8. The composite of claim 1 wherein the carrier sheet is comprised of 2 mil polyethylene film.

9. The composite of claim 1 wherein the upper surface of the film dressing has a matte finish.

10. The composite of claim 1 wherein the rigidity strip has an upper surface and a lower adhesive surface, the upper surface adhered to the lower adhesive surface of the film dressing.

11. The composite of claim 10 wherein the rigidity strip is further comprised of the same material as the film dressing, and the lower adhesive surface of the rigidity strip is further comprised of the same material as the lower adhesive surface of the film dressing.

12. A wound dressing composite comprising:

a membrane film wound dressing, made of polyurethane with a moisture vapor transmission rate of at least 20 grams per 100 square inches per 24 hours, having an upper surface, a lower adhesive surface and opposed side edges for application in a spread out disposition to a wound site with the lower surface adhered thereto, said film dressing substantially unable to support itself in a planar configuration;

a relatively stiff substantially transparent carrier sheet, made of polyethylene film, having an upper surface, a lower surface, and opposed side edges, the carrier sheet being releasably adhered on its lower surface to the upper surface of the film dressing in supporting relation for supporting the film dressing in a planar configuration with the side edges of film dressing and carrier sheet aligned in close adjacency;

at least one tab, made of paper, attached to the carrier sheet adjacent at least one of the opposed side edges thereof, the tab extending out beyond the side edge of the carrier sheet and adjacent a side edge of the film dressing for removing the carrier sheet from the film dressing after application thereof to the wound site;

at least one rigidity strip, made of the same material as the film dressing, in the form of a strip having a width that is relatively narrow compared to the width of the film dressing, and having a length that is substantially equal to the length of the film dressing, having an upper surface and a lower adhesive surface, the upper surface adhered to the lower adhesive surface of the film dressing along at least one of the side edges of the film dressing which underlies the tabs, for promoting adhesion between the film dressing and the wound site when the carrier sheet is removed from the film dressing;

a pad adhered to a center region of the adhesive lower surface of the film dressing;

a cover, made of paper coated with silicone, releasably adhered to the lower adhesive surface of the film dressing in covering relationship therewith for protecting the lower adhesive surface prior to application of the film dressing to the wound site; and the sheet dressing composite having a generally rectangular shape.

13. The composite of claim 12 wherein the lower adhesive surfaces of the film dressing and the rigidity strip are made of a hypoallergenic acrylate copolymer.

14. The composite of claim 12 wherein the upper surface of the film dressing has a matte finish.

15. A wound dressing composite which comprises:

a breathable membrane film wound dressing having a thickness of from about 0.80 mils to about 1.20 mils, a moisture vapor transmission rate (MVTR) greater than about 20 grams/100 in$^2$/24 hours at 100° F. and 90% relative humidity as measured by ASTM E96 Method E and having an upper surface, a lower adhesive surface and opposed side edges for application in a spread out disposition to a wound site with the lower surface adhered thereto, said film dressing substantially unable to support itself in a planar configuration;

a relatively stiff substantially transparent integral carrier film having an upper surface, a lower surface, and opposed side edges, the carrier film being releasably adhered on its lower surface to substantially the entire upper surface of the film dressing in supporting relation for supporting the entire film dressing in a planar configuration;

tabs substantially fixedly attached to the carrier sheet adjacent opposite side edges thereof, the tabs extending out beyond the side edges of the carrier sheet and adjacent side edges of the film dressing for removing the carrier sheet from the film dressing after application thereof to the wound site; and a cover releasably adhered to the lower adhesive surface of the film dressing in covering relationship therewith for protecting the lower adhesive surface prior to application of the film dressing to the wound site, said cover extending out beyond the side edges of the film dressing adjacent said tabs so that said tabs and the adjacent portions of said cover both extend out beyond the side edges of the film dressing in close face-to-face adjacency.

16. The composite of claim 15 further comprising at least one rigidity strip in the form of a strip having a width that is relatively narrow compared to the width of the film dressing, and having a length that is substantially equal to the length of the film dressing, having an upper surface and a lower adhesive surface, the lower adhesive surface adhered to the upper surface of the film dressing along at least one of the side edges of the film dressing which underlies the tabs, for promoting adhesion between the film dressing and the wound site when the carrier sheet is removed from the film dressing, wherein said rigidity strip is made of substantially the same material as said film dressing.

17. The composite of claim 15 wherein the carrier sheet is comprised of 2 mil polyethylene film.

18. The composite of claim 15 further comprising at least one rigidity strip in the form of a strip having a width that is relatively narrow compared to the width of the film dressing, said strip having a length that is a substantially equal to the length of the film dressing, having an upper surface and a lower adhesive surface, the upper surface adhered to the lower adhesive surface of the film dressing along at least one of the side edges of the film dressing which underlies a tab, for promoting adhesion between the film dressing and the wound site when the carrier sheet is removed from the film dressing, wherein said rigidity strip is made of the same material having substantially the same thickness as said film dressing.

19. The composite of claim 18 wherein the lower adhesive surface of the rigidity strip is further comprised of the same material as the lower adhesive surface of the film dressing.

20. A method for applying a wound dressing composite wherein the composite comprises:

a breathable membrane film wound dressing having a thickness of from about 0.80 mils to about 1.20 mils, a moisture vapor transmission rate (MVTR) greater than about 20 grams/100 in$^2$/24 hours at 100° F. and 90% relative humidity as measured by ASTM E96 Method E and having an upper surface, a lower adhesive surface and opposed side edges for application in a spread out disposition to a wound site with the lower surface adhered thereto, said film dressing substantially unable to support itself in a planar configuration;

a relatively stiff substantially transparent carrier film having an upper surface, a lower surface, and opposed side edges, the carrier film being releasably adhered on its lower surface to substantially the entire upper surface of the film dressing in supporting relation for supporting the entire film dressing in a planar configuration;

tabs substantially fixedly attached to the carrier sheet adjacent opposite side edges thereof, the tabs extending out beyond the side edges of the carrier sheet and adjacent side edges of the film dressing for removing the carrier sheet from the film dressing after application thereof to the wound site; and a cover releasably adhered to the lower adhesive surface of the film dressing in covering relationship therewith for protecting the lower adhesive surface prior to application of the film dressing to the wound site, said cover extending out beyond the side edges of the film dressing adjacent said tabs so that said tabs and the adjacent portions of said cover both extend out beyond the side edges of the film dressing in close face-to-face adjacency, the method comprising removing the cover from the lower adhesive surface of the film dressing, applying the film dressing over a wound site and removing the carrier film from the film dressing by grasping at least one of the tabs fixedly attached to the carrier film and separating the carrier film from the dressing.

21. The method of claim 20 wherein the cover contains two inwardly overlapping sections, the method further comprising removing the cover by grasping the overlapping sections of the cover and pulling apart the sections so as to remove the cover from the composite thereby exposing the lower adhesive surface of the dressing.

22. The method of claim 20 further comprising pressing substantially the entire upper surface of the carrier film prior to separating the carrier film from the dressing thereby smoothing and adhering the film dressing to the wound site.

23. The method of claim 22 wherein the composite further comprises a rigidity strip having a width which is relatively narrow compared to the width of the film dressing and having a length substantially equal to the length of the film dressing said strip being made of substantially the same material and having substantially the same thickness as the film dressing and being adjacent an edge of the film dressing along the side edge of the film dressing which is adjacent to and which underlies a portion of at least one tab, the method further comprising pressing the portion of the tab overlaying the rigidity strip to promote adhesion between the film dressing and the wound site.

24. The method of claim 20 wherein the composite further comprises a rigidity strip having a width which is relatively narrow compared to the width of the film dressing and having a length substantially equal to the length of the film dressing said strip being made of substantially the same material and having substantially the same thickness as the film dressing and being adjacent an edge of the film dressing along the side edge of the film dressing which is adjacent to and which underlies a portion of at least one tab, the method further comprising pressing the portion of the tab overlaying the rigidity strip to promote adhesion between the film dressing and the wound site before separating the carrier film from the dressing.

25. The method of claim 24 wherein the carrier film is separated from the dressing by grasping the tab overlaying the rigidity strip.

* * * * *